United States Patent [19]

Levandoski

[11] Patent Number: 4,892,480

[45] Date of Patent: Jan. 9, 1990

[54] FACE BOW

[76] Inventor: Ronald R. Levandoski, 1103 Powell Ave., Erie, Pa. 16505

[21] Appl. No.: 244,098

[22] Filed: Sep. 14, 1988

[51] Int. Cl.4 .............................................. A61C 19/04
[52] U.S. Cl. ...................................................... 433/73
[58] Field of Search ......................... 433/73, 56, 68, 69

[56] References Cited

U.S. PATENT DOCUMENTS 4,695,252  9/1987  Edwardson ........................... 433/73

Primary Examiner—Robert Peshock
Attorney, Agent, or Firm—Charles L. Lovercheck; Wayne L. Lovercheck; Dale R. Lovercheck

[57] ABSTRACT

A face bow for use with an articulator. The face bow has a caliper having ends to engage the ear area of a patient to support the articulator, a naison suture engaging means to engage the nose area of the patient and a fork to engage the teeth of a patient. Adjusting means to adjust the position of the naison indicator engaging means, the auditory meatus engaging means and the fork relative to each other. The face bow being adapted to be transferred to an articulator for use in adjusting dental models on the articulator.

10 Claims, 3 Drawing Sheets

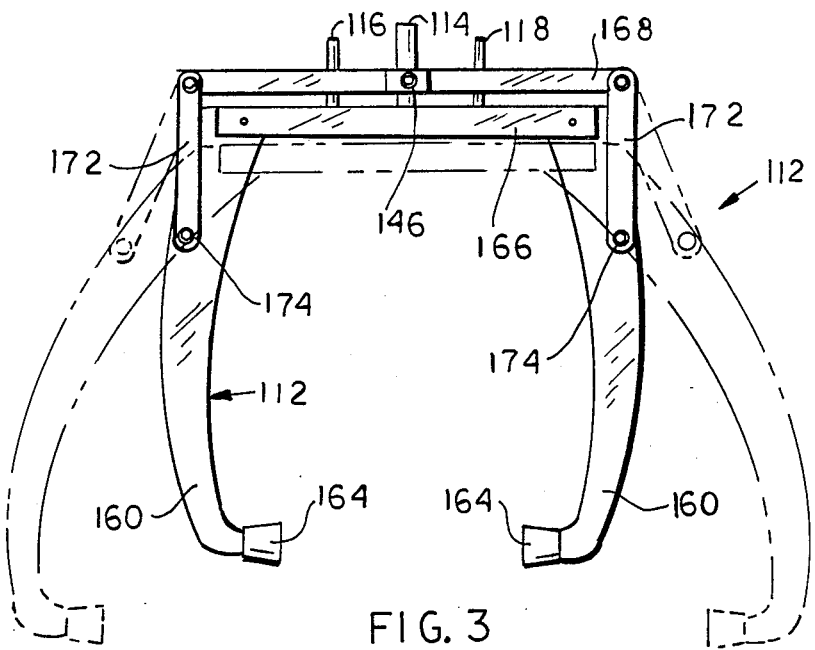
FIG. 3
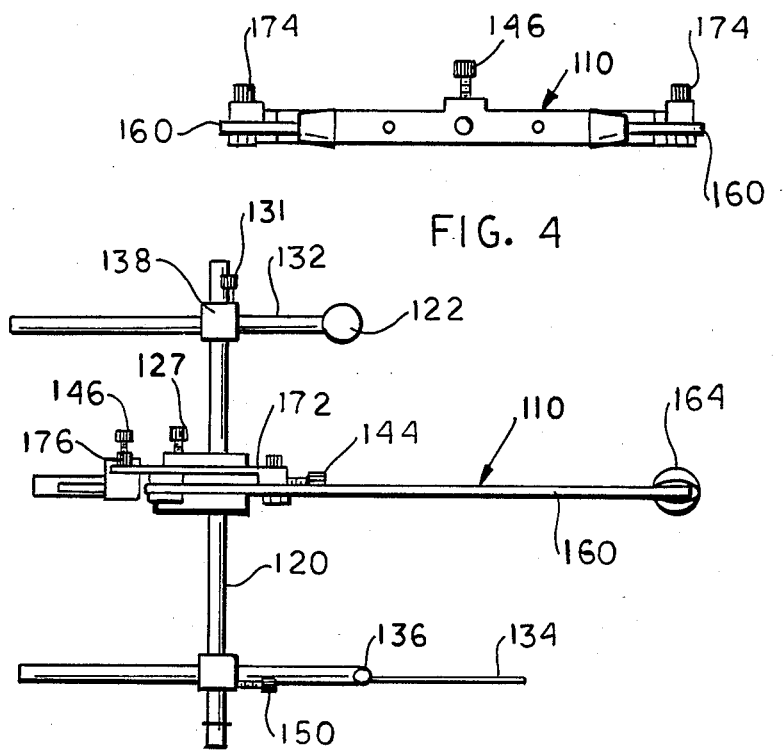
FIG. 4
FIG. 5

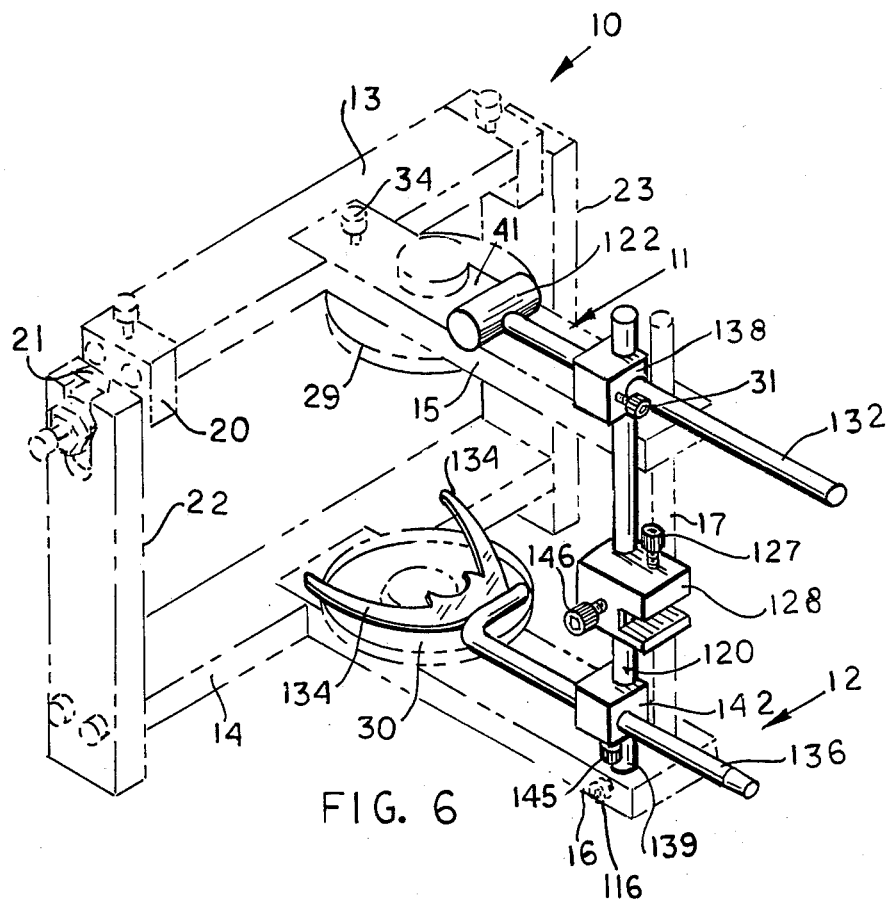
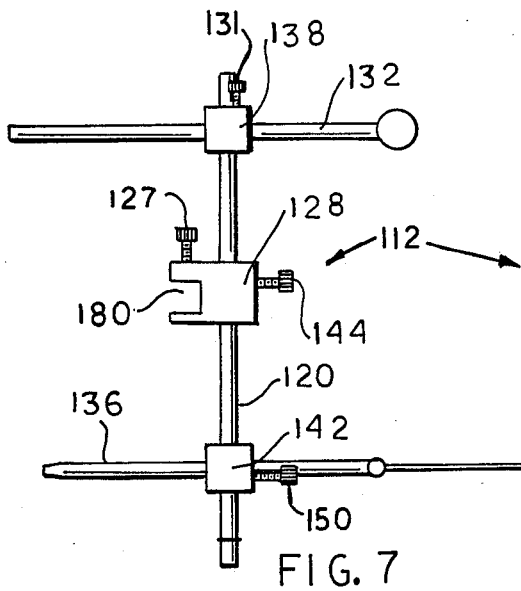
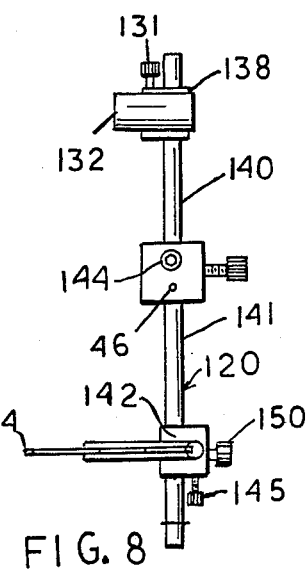
FIG. 6
FIG. 7
FIG. 8

4,892,480

FACE BOW

BACKGROUND OF THE INVENTION

The invention relates to means for mounting dental models, an attached caliper means and an articulator to permit adjustment of the articulator to a record. The invention also relates to a method for using the mounting means.

In dental restoration appliances are fabricated from models mounted on dental articulators which have provided varied capability in simulation of mandibular movement. Recent advances in articulator design have achieved precision instruments which can be adjusted for most, if not all, manidbular movements and TMJ space compression with the aid of devices for recording of mandibular movement such as checkbite records, face bows, hinge axis locators, etc.

The face bow disclosed herein incorporates a caliper like device that relates the position of the posterior area of the mandibular condyles at the level of the auditory meatus to the maxillary teeth. The face bow disclosed consists of a unique arrangement for adjusting the calipers consisting of three rods for stability and locking in their final adjustment. The calipers, in turn, provide support for a vertical main rod which has a cylindrical attachment (naison indicator) that engages the bridge of the nose over the naison suture and an adjustable, detachable, caliper support. This subassembly can be adjusted to help hold and support the calipers about the face. The vertical main rod is in turn used with a rod/fork assembly for engaging the maxillary teeth. After all measurements are obtained the calipers are removed at the detachable caliper support and the main rod is inserted into a round recess on the lower beam of the articulator. A nasion indicator is attached to the main rod of the articulator which allows recording the position of the soft tissue nasion from the facebow. A maxillary model of the patient's teeth is then placed on the rod/fork assembly and attached to the upper beam articulator ring with plaster. The lower model is related to the upper and attached to the lower beam with plaster.

Important features of this face bow are the basic design and the fact that the three rod adjustment supplies stability to the face bow and an infinite range of locking adjustment. The nasion rest is kept intact with the main rod and rod/fork of the face bow for the purpose of allowing the position of the nasion to be related to the maxillary models through additional attachments and assemblies on the articulator. Thus, through the use of a cephlometric radiograph, the soft tissue nasion can be related to other areas on models of the patient's teeth and/or gum tissues for the purpose of using cephlometric analysis to, for instance, set denture teeth and determine specific anchorage requirements for orthodontic cases, TMJ splint fabrication, bridge work, etc.

Fabrication of the final face bow appliance from filled plastics would allow the entire unit to be soaked in cold sterilizing solutions for cleaning purposes. Certain parts would be disposable to avoid cross contamination.

OBJECTS OF THE INVENTION

It is an object of the invention to provide an improved face bow.

Another object of the invention is to provide an improved method of relating a maxillary dental model to a lower dental model Another object of the invention to provide a face bow to be supported on the bridge of the nose and the ear cavities of a patient by calipers with a tooth engaging fork that is vertically plus horizontally adjustable and a naison indicator which is angularly adjustable to correspond to the patient's soft tissue naison which can be positioned and locked and used in combination with an articulator and related to maxillary models.

Another object of the invention is to provide a naison rod that can record the soft tissue naison which can then be recorded and transferred to the upper beam. From this point, you can position teeth natural (on models) or artificial (dentures) to cephalometric norms for treatment or diagnosis purposes.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

BRIEF DESCRIPTION OF THE DRAWINGS

FIG. 3 is a top view of the calipers removed from the face bow.

FIG. 4 is a front view of the calipers.

FIG. 5 is a side view of the face bow with calipers in place, according to the invention.

FIG. 6 is an isometric view of the face bow with calipers removed, shown supported on an articulator. The articulator is shown in phantom lines.

FIG. 7 is a side view of the facebow with calipers removed.

FIG. 8 is a rear view, partly in cross section, of the facebow.

DETAILED DESCRIPTION OF THE DRAWINGS

Figure 1:
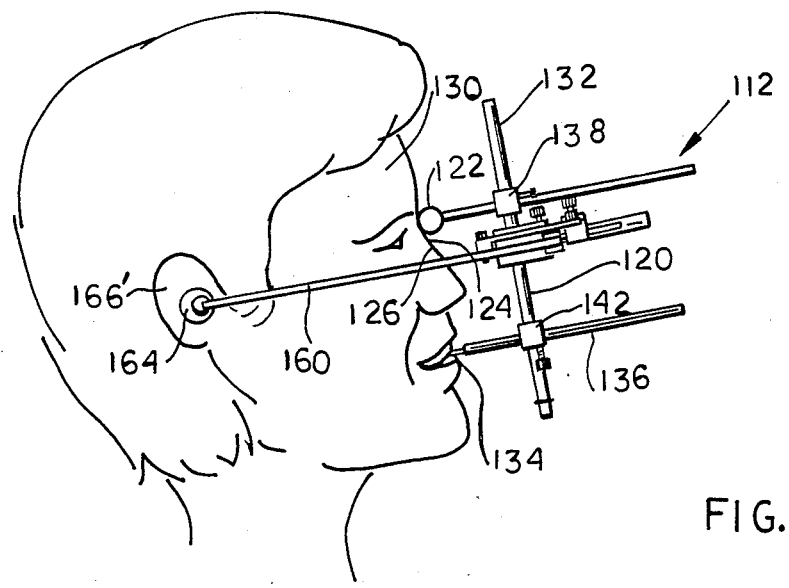
FIG. 1 is a side view of the face bow shown with calipers supported on the face of a patient.
Figure 2:
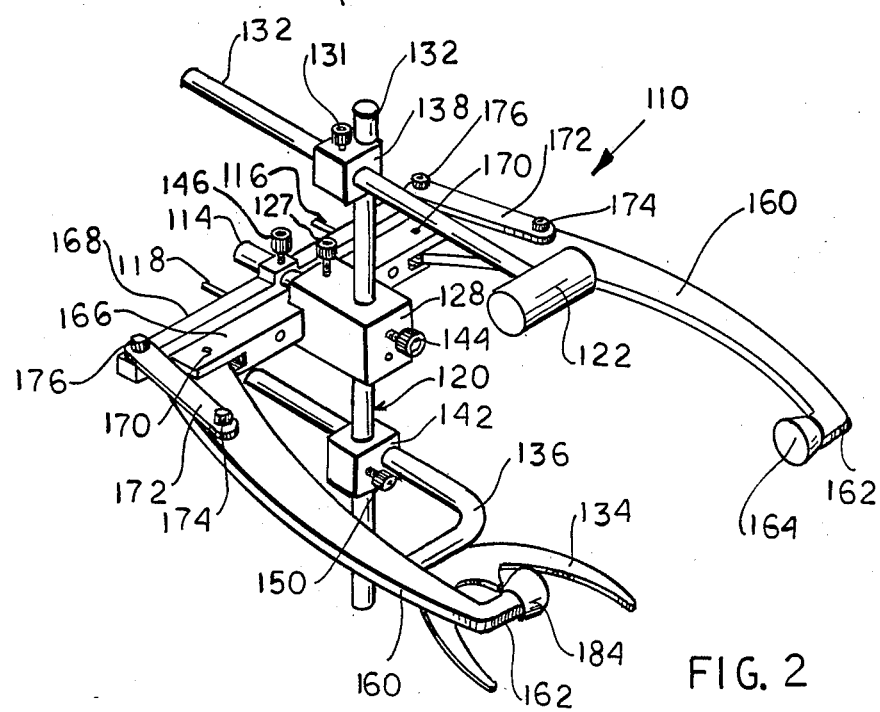
FIG. 2 is an isometric view of the face bow shown in FIG. 1 with the calipers in place.

Now with more particular reference to the drawings, the face bow indicated generally at 112 shown in FIGS. 1, 2 and 5 through 8 is supported on vertical support 120. Articulator 10, shown in FIG. 6, has upper frame 11 and lower frame 12. Upper frame 11 has upper beam 13. Upper beam 13 has flanges 20 and is pivoted to lower beam 14 by condyle pivot means 21, that are connected to vertical supports 22 and 23. Upper arm 15 is attached to upper beam 13. Laterally extending lower beam 14 has lower arm 16 fixed to it and extending forwardly from it, generally parallel to upper arm 15. Lower arm 16 has recess 139 therein which receives the lower end of rod 120. Incisal pin 17 on upper arm 15 engages lower arm 16 to limit the swinging movement of upper arm 15 toward lower arm 16.

A caliper support bracket 128, a nasion indicator support bracket 138 and a fork support bracket 142 are supported on vertically extending vertical support 120. In actual practice, vertically extending vertical support 120 can be made of two pieces 140 and 141 having their ends received in a vertical bore in caliper support bracket 128 and locked in place therein by suitable set screws 144 and 46.

Brackets 138, 128 and 142 may be locked against sliding and rotation and into position on vertical support 120 by means of set screws 31, 144 and 150.

Fork support rod 136 has teeth engaging fork means 134 supported on its end. Fork support rod 136 is held against sliding and rotation in fork support bracket 142 by means of set screw 145. Naison indicator cylinder 122 is supported on the outer end of naison indicator support rod 132 and is slidable and adjustable in bracket 138 and held against sliding by set screw 131.

Caliper 110 is shown in FIGS. 1, 2, 3 and 4. Caliper 110 has front beam 166, rear beam 168 and two spaced arms 160. Front beam 166 has a first end, a second end and an intermediate part. Rear beam 168 also has a first end, second end and an intermediate part. First beam 166 and second beam 168 are disposed in spaced parallel relation to one another and are maintained in this relation by rods 114, 116 and 118 when the beams are moved with arms 160. Rods 114, 116 and 118 are fixed to front beam 166 at their forward ends and have their rearward ends extending outward through bores in rear beam 168. Set screw 146 threadably locks rear beam 168 to rod 114 in fixed position when arms 160 are adjusted to the proper spacing relative to each other. Set screw 146 could be located to engage either of rods 114, 116 or 118 without changing the function.

Links 172 each have a first end and a second end. The first end of each link 172 is pivotally connected to an end of rear beam 168 by one of the pivots 176. The front end of links 172 are each pivoted to an intermediate part on arms 160 by pivots 174.

Arms 160 are swingably connected to front beam 166 by pivot 170. Thus when the auditory meatus engaging members 184 engage the auditory meatus of a patient, when the face bow is supported on the patient's face, as shown in FIG. 1, the beams 166 and 168 will be moved away from each other to a particular point and can be locked by screw 146. The naison indicator 122 can then be adjusted to engage the bridge of the patient's nose and the teeth engaging fork means 134 adjusted to rest on the patient's teeth.

Slot 180 is formed in the rear edge of caliper support bracket 128. Screw 127 can be loosened to unlock front beam 166 of calipers 112 and the face bow removed from the calipers.

In use, the face bow will first be supported on the face of a patient as described above, as shown in FIG. 1, and arms 160 will be adjusted by loosening screw 146 and moving members 184 into the auditory meatus of the patient. Screw 146 will be locked then preventing rod 114 from sliding in rear beam 168 and arms 160 from moving. The operator will then adjust fork support rod 136 toward or away from the patient's face until teeth engaging fork means 134 rests on the teeth of the patient and tighten the screw 148, thereby positioning teeth engaging fork means 134. Screw 131 will then be loosened and naison indicator cylinder 122 will be brought to rest on the bridge of the patient's nose over the naison suture of the patient above the bridge 126 of the patient's nose. The naison support rod 132 will then be locked into position by tightening screw 131.

After all measurements are obtained, the calipers 112 will then be removed from the face bow by loosening screw 127 and the face bow 110 will then be transferred to the articulator 10, shown in FIG. 6. The lower end of vertical support 120 will then be placed in the face bow support means or aperture 139 in the lower arm 12 of the face bow and screw 116 will be tightened, clamping the face bow in place on articulator 10.

Naison index 31 is supported on first denture support 29, which allows recording the position of the naison indicator 122 on the face bow. First denture support 29 is adjusted to bring naison index 31 into engagement with naison indicator 122. A maxillary model of the patient's teeth is then placed on teeth engaging fork means 134 and attached to first denture support 29 of the articulator with plaster. The lower model is then placed on second denture support 30 and articulated to the lower maxillary model on the upper model support in accordance with the procedures explained in U.S. Pat. No. 4,668,189 to Levandoski.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. In combination a face bowl and an articulator,
    said face bow comprising a vertically extending rod,
        a first bracket, a second bracket, and a third bracket,
    said first bracket, said second bracket and said third bracket each being vertically adjustably and slidably received on said vertically extending rod,
    a teeth engaging fork means having a first support rod attached thereto and slidably received in first bracket,
    a naison indicating member having a second support rod attached thereto,
    said second support rod being slidably horizontally an adjustably supported on said third bracket,
    said calipers removably supported on said second bracket,
    said calipers having auditory meatus engaging means thereon whereby said calipers can be supported on the auditory meatus of a patient, thereby supporting said face bow on said patient,
    said articulator having an upper frame and a lower frame, a first denture support on said upper frame, a second denture support on said lower frame aNd condyle means,
    said condyle means swingably supporting said second denture support relative to said first denture support,
    said calipers being adapted to be removed from said second bracket and said face bow transferred to said articulator,
    a face bow recess means on said lower frame of said articulator for receiving a part of said vertical support,
    said vertical support rod having a part adapted to be received in said recess means whereby said face bow is supported on said articulator,
    said first denture support having means thereon to adjust said first denture support relative to said naison indicator,
    said second denture support being adapted to be adjusted to conform to said teeth engaging fork means on said articulator to position said denture supports relative to one another to be articulated on said articulator.

2. The combination recited in claim 1 wherein
said adjusting means on said third bracket comprises an opening in said third bracket slidably receiving said tooth engaging member supporting rod.

3. The combination recited in claim 2 wherein said third bracket has an opening therein slidably receiving said vertical support and means to lock said third bracket in vertically adjusted position on said vertical support rod.

4. The combination recited in claim 2 wherein said second bracket has an opening therein receiving said vertical support and means to lock said second bracket against sliding on said vertical support.

5. The combination recited in claim 3 wherein said third bracket has a screw to lock said tooth engaging fork means in vertically adjusted postion on said vertical support.

6. The combination recited in claim 5 wherein said calipers comprises a first arm and a second arm,
said first arm and said second arm each having a first end and a second end,
first beam and a second beam, each having a first end and a second end,
said first end of said first arm having auditory meatus engaging means,
said first end of said second arm having auditory meatus engaging means,
said second end of said first arm being swingably attached to said first end of said first beam,
said second end of said second arm being swingably attached to said second end of said first beam,
a first link having a first end and a second end,
a second link having a first end and a second end,
said second bar having a first end and a second end,
said first end of said first link being swingably attached to said first end of said first arm,
said first end of said second link being swingably attached to said second end of said second beam,
said second end of said first link being swingably connected to said first arm of said caliper at a point between said first end and said second end of said first arm,
said second end of said second link being swingably attached to said second arm at a point between said first end and said second end of said second arm,
said second end of said second link being swingably attached to said second end of said second beam whereby said auditory meatus means can be swung toward and away from one another with said arms.

7. The combination recited in claim 6 wherein said caliper is attached to said second bracket by means of a slot in said second bracket,
said slot receiving an intermediate part of said first beam between said first end and said second end thereof,
and a screw threadably engaging said first bracket and adapted to engage said first beam holding said first beam in position in said slot.

8. The combination recited in claim 6 wherein said first beam and said second beam are disposed generally parallel to one another and means on said first beam slidably engaging said second beam for guiding said second beam in a movement of translation relative to said first beam.

9. A method of articulating a set of dentures for a patient including a first denture member and a second denture member,
said method comprising,
providing an articulator and a face bow, having a vertical support and a tooth engaging means, a naison indicator and calipers supported on said vertical support by a first bracket, a second bracket and a third bracket respectively,
said calipers being removably supported on said vertical support,
said calipers having auditory meatus engaging means thereon,
said articulator having a first denture support and means for swingably supporting said upper frame on said lower frame and a second denture support supported on said upper frame,
said method including:
supporting said face bow on said calipers by said second bracket,
supporting said calipers on the auditory meatus of said patient,
adjusting said auditory meatus engaging means to bring said naison indicating means into engagement with the naison suture of said patient by means of said second bracket,
adjusting said teeth engaging means by means of said first bracket to bring said teeth engaging means into engagement with the teeth of said patient by means of said first bracket,
adjusting said naison indicator into engagement with the nose of said patient by means of said a third bracket,
removing said face bow from said calipers and supporting said face bow on said articulator,
adjusting said first denture support on said articulator to bring said naison index into engagement with said naison indicating means on said face bow,
supporting a first denture on said first denture support,
supporting a second denture on said second denture support,
adjusting said second denture support on said articulator to bring said second denture support into engagement with said naison indicating means,
articulating said first denture and said second denture relative to one another.

10. The face bow recited in claim 1 wherein said third bracket and said first bracket are adjustably supported on said vehicle support by means of a first vertical hole in said first bracket, a second vertical hole in a said second bracket and a third vertical hole in said third bracket,
said vertical holes in each said bracket slidably receiving said vertical support and said horizontal hole in said third bracket slidably receives said fork support rod and a horizontal hole in said first bracket slidably receiving said naison support rod.

* * * * *